United States Patent
Komatsu et al.

(10) Patent No.: US 8,384,021 B2
(45) Date of Patent: Feb. 26, 2013

(54) METHOD OF FORMING MASS IMAGE

(75) Inventors: Manabu Komatsu, Kawasaki (JP); Hiroyuki Hashimoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/255,094

(22) PCT Filed: Mar. 30, 2010

(86) PCT No.: PCT/JP2010/056120
§ 371 (c)(1),
(2), (4) Date: Sep. 6, 2011

(87) PCT Pub. No.: WO2010/116961
PCT Pub. Date: Oct. 14, 2010

(65) Prior Publication Data
US 2011/0315871 A1    Dec. 29, 2011

(30) Foreign Application Priority Data
Apr. 10, 2009    (JP) ................................ 2009-096091

(51) Int. Cl.
*H01J 49/00* (2006.01)
*G01N 33/00* (2006.01)
*G01N 24/00* (2006.01)

(52) U.S. Cl. ........................... 250/282; 436/173; 436/86

(58) Field of Classification Search ................... 250/282; 436/173, 86
See application file for complete search history.

(56) References Cited

U.S. PATENT DOCUMENTS

| | | | |
|---|---|---|---|
| 7,446,309 B2 | 11/2008 | Murayama et al. | |
| 7,714,280 B2 | 5/2010 | Komatsu et al. | |
| 7,759,130 B2 * | 7/2010 | Oda et al. | 436/173 |
| 7,795,579 B2 | 9/2010 | Komatsu et al. | |
| 7,956,321 B2 * | 6/2011 | Murayama et al. | 250/282 |
| 8,084,214 B2 | 12/2011 | Hashimoto et al. | |
| 2001/0021535 A1 * | 9/2001 | Nelson et al. | 436/518 |
| 2007/0105087 A1 | 5/2007 | Ban et al. | |
| 2008/0090267 A1 * | 4/2008 | Komatsu et al. | 435/29 |
| 2008/0278706 A1 | 11/2008 | Murayama et al. | |
| 2009/0093373 A1 | 4/2009 | Kawaguchi et al. | |
| 2010/0273863 A1 * | 10/2010 | Corey et al. | 514/44 R |

FOREIGN PATENT DOCUMENTS

| | | |
|---|---|---|
| JP | 2004-37120 A | 2/2004 |
| JP | 2008-304366 A | 12/2008 |

OTHER PUBLICATIONS

PCT International Search Report and Written Opinion of the International Searching Authority, International Application No. PCT/JP2010/056120, Mailing Date Apr. 27, 2010.

(Continued)

*Primary Examiner* — Robert Kim
*Assistant Examiner* — Kevin Chung
(74) *Attorney, Agent, or Firm* — Fitzpatrick, Cella, Harper & Scinto (57) ABSTRACT

An object of the present invention is to provide a method of comprehensively visualizing a constituent in tumor tissue or the like at a cellular level.

The present invention provides a method of forming a two-dimensional distribution image of a target constituent based on information on the mass of constituents of the tissue section wherein, as the internal standard material, any one of actin, tubulin and GAPDH is used in the intracellular region, one of histone and nucleic acid is used in the nuclear region, and one of albumin and cytokine is used in the extracellular region.

3 Claims, 5 Drawing Sheets

OTHER PUBLICATIONS

Ostrowski, et al., "Secondary Ion MS Imaging to Relatively Quantify Cholesterol in the Membranes of Individual Cells from Differentially Treated Populations", Anal. Chem, vol. 79, No. 10, 2007, pp. 3554-3560.

Fletcher, et al., "A New Dynamic in Mass Spectral Imaging of Single Biological Cells", Anal. Chem, vol. 80, No. 23, 2008, pp. 9058-9064.

Johansson, et al., "ToF-SIMS imaging of lipids in cell membranes", Surface and Interface Analysis, vol. 38, 2006, pp. 1401-1412.

Berman, et al., "Preparation of Single Cells for Imaging/Profiling Mass Spectrometry", J. Am. Soc. Mass Spectrom, vol. 19, 2008, pp. 1230-1236.

Yamada, et al., "A Processing Technique for Cell Surfaces Using Gas Cluster Ions for Imaging Mass Spectrometry", J. Mass Spectrom. Soc. Jpn., vol. 57, No. 3, 2009, pp. 117-121.

Monroe, et al., "Vitamin E Imaging and Localization in the Neuronal Membrane", J. Am. Chem. Soc., vol. 127, No. 35, 2005, pp. 12152-12153.

* cited by examiner

145-163
127-145
109-127
91-109
73-91
55-73
37-55
19-37
1-19
NORMALIZED COUNTS

METHOD OF FORMING MASS IMAGE

TECHNICAL FIELD

The present invention relates to a method of acquiring information on the mass of constituents in an analyte as an image using mass spectrometry, and particularly to a method of forming an image of the two-dimensional distribution state of a biological substance such as proteins and peptides contained in a tissue section by normalizing signal strength.

BACKGROUND ART

There is known an analytical method of comprehensively visualizing the expression amount of a protein expressed in tumor tissue based on signal strength using a time-of-flight secondary ion mass spectrometer (TOF-SIMS) (U.S. Pat. No. 7,446,309).

Moreover, the normalization of signal intensity of mass spectrometry using a standard material is known. In a proteomic analysis, proteins are separated by two-dimensional electrophoresis and the separated proteins are analyzed by mass spectroscopy. Then, the intensity of the protein of interest is normalized using the intensity of a protein having a known content as a standard to obtain a quantitative result.

A two-dimensional distribution image of a target protein can be formed based on the signal intensity of target proteins by using such as TOF-SIMS and matrix-assisted laser desorption-ionization mass spectrometry (MALDI-MS). In such cases, there is known a method of normalizing the signal intensity using the total doses of primary ions, the irradiance of a pulse laser, or the resulting number of total counts of secondary ions as a standard.

The normalization using an external standard material is also proposed. Here, the external standard material refers to a standard material for normalizing the mass signal intensity obtained by mass spectroscopy, which is not contained in a measurement sample but added to the sample. The use of external standard material in TOF-SIMS is shown in Japanese Patent Application Laid-Open No. 2004-037120. In the publication, a material used as an external standard is arranged outside the measurement range of a sample. Then the signal intensity of the protein of interest in the sample is normalized by the signal intensity of the external standard. By this method, the signal intensities of the sample and the external standard can be obtained in a same condition.

The use of external standard material in MALDI-MS is also known. For example, it is known that a certain amount of specific peptide is mixed with a matrix agent and that the matrix is uniformly sprayed on a sample surface so as to use the peptide as an external standard to obtain a two-dimensional distribution image of the mass spectrum of constituents of a tissue section.

The normalization using an internal standard is also proposed. Here, the internal standard material refers to a standard material for normalizing the mass signal intensity obtained by mass spectroscopy, which is previously contained in a measurement sample. For example, in S. G. Ostrowski et al., Anal. Chem. 79, 3554 (2007), the signal intensity of cholesterol in a cell membrane surface is normalized using the signal intensity of the fragment ion obtained from a lipid component of the cell as a standard to form a two-dimensional distribution image by TOF-SIMS.

DISCLOSURE OF THE INVENTION

In Japanese Patent Application Laid-Open No. 2004-037120, since an external standard material is arranged in a position away from the target constituent, it was difficult to correct a local sensitivity variation resulting from an ionization inhibiting substance such as salt and lipid locally present in a measurement range.

In S. G. Ostrowski et al., Anal. Chem. 79, 3554 (2007), cultured cells were subjected to two-dimensional distribution measurement and the signal of the fragment ion ($C_5H_9^+$) of a lipid molecule on the cell membrane is used as an internal standard in each pixel in an image. However, the lipid molecule used for the internal standard has a biased two-dimensional distribution according to the shape of the cell membrane. For example, in nucleus or outer cells of a tissue section, the lipid molecule is seldom present. Therefore, the normalized signal was calculated as a higher value than the signal corresponding to the actual abundance. For this reason, it was difficult to form an image appropriately reflecting the abundance of a measurement object when a two-dimensional distribution image was formed.

As a result of intensive study for solving the above-described problems, the present inventors have achieved the present invention.

The present invention relates to a method of forming a two-dimensional distribution image of a target constituent in constituents of a tissue section based on information on the mass of constituents of the tissue section including; determining a region to which the constituents belong to be at least one of an intracellular region, a nuclear region, and an extracellular region, calculating, for each region determined in the previous region determination, a normalized intensity of the mass derived from the target constituent from a mass signal intensity derived from the target constituent in a mass spectrum of the constituents and a mass signal intensity derived from an internal standard material in the constituents, and forming the two-dimensional distribution image of the target constituent based on the normalized intensity of the mass derived from the target constituent, wherein, as the internal standard material, (i) any one of actin, tubulin, and GAPDH is used in the intracellular region, (ii) one of histone and nucleic acid is used in the nuclear region, and (iii) one of albumin and cytokine is used in the extracellular region.

According to the present invention, when a two-dimensional distribution image based on information on the mass of constituents in an analyte is acquired, it is possible to obtain a signal intensity in which variations such as sensitivity difference in the case of mass spectroscopy has been corrected for each pixel. In addition, since an internal standard is selected by the region to which a pixel belongs, a more suitable internal standard is selected. Therefore, distribution of the normalized signal intensity matches the actual distribution of the constituent.

Further features of the present invention will become apparent from the following description of exemplary embodiments with reference to the attached drawings.

BEST MODES FOR CARRYING OUT THE INVENTION

The present invention relates to a method of forming a two-dimensional distribution image of a target constituent in the constituents of a tissue section, based on information on the mass of constituents of a tissue section, including the steps of; determining a region to which the constituents belong to be at least one of an intracellular region, a nuclear region, and an extracellular region, calculating, for each region determined in the previous step, a normalized intensity of the mass derived from the target constituent from a mass signal intensity derived from the target constituent in a mass spectrum of the constituents and a mass signal intensity derived from an internal standard material in the constituents, and forming the two-dimensional distribution image of the target constituent based on the normalized intensity of the mass derived from the target constituent, wherein, as the internal standard material, (i) any one of actin, tubulin, and GAPDH is used in the intracellular region, (ii) one of histone and nucleic acid is used in the nuclear region, and (iii) one of albumin and cytokine is used in the extracellular region.

The method of the present invention is a method of acquiring information on the mass of constituents in an analyte using mass spectrometry and forming a two-dimensional distribution image of a target constituent based on the acquired information on mass. The method can be performed by the following steps;

(1) The step of determining a measurement range of an analyte;

(2) The step of dividing the measurement range into pixels;

(3) The step of obtaining a mass spectrum of the pixels by mass spectrometry;

(4) The step of determining a region to which the pixels belong;

(5) The step of determining an internal standard material for mass spectroscopy of the pixels;

(6) The step of calculating the normalized intensity of the mass derived from a target constituent from the signal intensity of the mass derived from the target constituent in the mass spectrum of the pixels and the signal intensity of the mass derived from an internal standard material; and (7) The step of constructing a two-dimensional distribution image in the measurement range of the normalized intensity of the mass derived from the target constituent.

Hereinafter, each step will be described in detail.

(1) The Step of Determining a Measurement Range of an Analyte

The measurement range is determined by observing an analyte. A unit for observation is not particularly limited, but a microscope attached to a mass spectrometer, an optical microscope, and the like can be used. A fluorescence microscope may be used when a target is a tissue section to which fluorescent-staining treatment is applied.

When a microscope attached to a mass spectrometer is used, a sample is, for example, first observed at low magnification, and during the observation a stage on which the sample is placed is displaced so as to roughly determine the measurement range to be observed. Then, the sample can be observed at high magnification to finely adjust so that a target cell may be contained in the measurement range.

Note that, in the present invention, an analyte is a tissue section and the measurement range is generally at a cellular level. The "cellular level" means the level that can at least identify an individual cell. The diameter of a cell is generally in the range of 10 μm to 20 μm, and a large cell such as a nerve cell has a diameter of about 50 μm. Therefore, for the observation in the present step, the spatial resolution needs to be 10 μm or less, and is preferably 5 μm or less, more preferably 2 μm or less, still more preferably 1 μm or less.

(2) The Step of Dividing the Measurement Range into Pixels

The length of one side of each pixel needs to be 10 μm or less, preferably 5 μm or less, more preferably 2 μm or less, still more preferably 1 μm or less.

When the analyte is observed under a microscope attached to a mass spectrometer, division into pixels can be performed by selecting the number of pixels to be measured on software. The number of pixels can be selected, for example, from the group consisting of 64×64, 128×128, 256×256 and 512×512 pixels.

Note that a plurality of two-dimensional data may be referred through the whole step, and in order to match the pixels in each data, two-dimensional coordinates can be set in each two-dimensional data.

(3) The Step of Obtaining a Mass Spectrum of the Pixels by Mass Spectrometry

Using a mass spectrometer, the measurement range of an analyte is subjected to comprehensive two-dimensional mass spectroscopy to obtain a mass spectrum corresponding to the pixels. When performing the steps (1) and (2) using a microscope and software attached to a mass spectrometer, it is possible to automatically obtain a mass spectrum for each pixel in the present step. On the other hand, when not performing the steps (1) and (2) using a microscope and software attached to a mass spectrometer or when required, each pixel needs to be corresponded to each other in each two-dimensional data. The number of the mass spectra obtained per pixel may be one or more. When a plurality of mass spectra is obtained, any one of them may be used or the plurality of spectra may be averaged.

The measurement conditions for mass spectroscopy may be previously determined or may be determined each time. The irradiation region of a primary probe of the mass spectroscopy is preferably smaller than the area of each pixel determined in the step (2). Preferably, it is also possible to obtain a two-dimensional distribution image of the mass spectrum which is sufficiently fine to the extent that the two-dimensional distribution image allows to distinguish whether the region of each pixel belongs, for example, to one of intracellular, extracellular, and nuclear regions. For this purpose, the aperture of the primary probe and lens system voltage may be manually or automatically controlled.

Note that the mass spectrometer used in the present step is not particularly limited. Hereinafter, a mass spectrometer will be described in detail.

The mass spectrometer for performing mass spectrometry generally has a sample-introducing part for ionizing a sample and an analyzing part for analyzing the ionized sample. The mass spectrometry can be classified into various analysis methods according to the system of the analyzing part.

Here, the method of ionization in the sample-introducing part includes the following methods:
(i) A method of using primary ions;
(ii) A FAB (Fast Atom Bombardment) method; and
(iii) A MALDI (Matrix Assisted Laser Desorption Ionization) method.

Here, the FAB method refers to a method in which a sample is mixed with a matrix, and neutral atoms are allowed to collide with the resulting mixture at high speed to ionize the sample.

The MALDI method refers to a method in which a sample is mixed with a matrix to produce a crystal, which is irradiated with a laser to ionize the sample.

The system of the analyzing part includes the following methods:
(i) Quadrupole type;
(ii) Magnetic deflection type;
(iii) Fourier transform ion cyclotron resonance type;
(iv) Ion trap type;
(v) Time-of-flight secondary ion mass spectroscopy (TOF-SIMS) type; and
(vi) Tandem type.

Here, the (i) quadrupole type refers to an analysis method in which ions are passed through four electrodes and high frequency voltage is applied to the electrodes to thereby cause perturbation in the sample to pass only a target ion;
(ii) The magnetic-deflection type refers to an analysis method of passing ions through a magnetic field and using the change of the flight path of the ions by the Lorentz force applied to the ions in the magnetic field;
(iii) The Fourier transform ion cyclotron resonance type refers to an analysis method in which ions are introduced into a cell to which an electrostatic field and an static magnetic field has been applied, and high frequency voltage for exciting ion motion is applied to detect the orbital period of the ions, and the mass is calculated from the cyclotron conditions;
(iv) The ion trap type refers to an analysis method in which ions are held in a trap chamber composed of electrodes and the electric potential thereof is changed to thereby selectively release the ions to separate these ions; and
(vi) The tandem type refers to a method of combining two or more of the above analysis methods.

The (v) time-of-flight secondary ion mass spectrometry (TOF-SIMS method) using primary ions for ionization may be preferably used. The TOF-SIMS method is a method capable of measuring a very small amount of sample with a high degree of accuracy in mass spectrometry. In addition, since a sample is ionized by pulsewise irradiation of a sample surface with primary ions, damage to the sample can be reduced and distribution information on a target component can be obtained correctly.

In the TOF-SIMS method, ionization of a sample is performed by irradiating it with primary ions. As a primary ion species, it is possible to use not only general liquid metal ions such as gallium ions ($Ga^+$) but also cluster ions such as trimer gold ions ($Au_3^+$) and trimer bismuth ions ($Bi_3^+$), from the viewpoint of ionization efficiency, mass resolution, and the like. Note that Bi ions are preferably used in that analysis can be performed with very high sensitivity.

In the TOF-SIMS method, secondary ions are generated from the face side of a component by the incidence of primary ions. During the analysis by the TOF-SIMS method, a several kV of electric field is applied between the component and a time-of-flight secondary ion mass spectrometer, and the secondary ions are taken into a detector by the electric field for analysis.

In imaging using TOF-SIMS, conditions such as mass resolution, analysis area, and measurement conditions such as primary ion pulse frequency, primary ion beam energy, and primary ion pulse width are closely related to imaging capability. For this reason, preferred analysis conditions are not uniquely decided. However, each set value of the measurement conditions is required to be within a certain range from the viewpoint that the analysis is possible. In the present invention, the primary ion beam pulse frequency is preferably in the range of from 1 kHz to 50 kHz. The primary ion beam energy is preferably in the range of from 12 keV to 25 keV, and the primary ion beam pulse width is preferably in the range of from 0.5 ns to 10 ns. The ion mass signal intensity in each pixel can be obtained by repeatedly scanning the primary ion beam 16 to 512 times on a pixel surface of 64 to 512 pixel square in a measurement range of 10 μm to 500 μm square. The signal intensity in each pixel in the specific mass number obtained here can be taken out and arranged according to each coordinate to obtain an image.

Similarly, when imaging using MALDI, preferred analysis conditions are not uniquely decided but each value is within a certain range. In the present invention, the pulse laser frequency is preferably in the range of from 1 Hz to 200 Hz. The pulse laser energy is preferably in the range of from 10 to 300 mW, and the pulse laser pulse width is preferably in the range of from 0.5 ns to 10 ns. In the case of MALDI, the mass signal of each pixel is obtained by moving a sample stage by 1 μm unit to scan the irradiation position of a pulse laser. The ion mass signal intensity in each pixel can be obtained by scanning the sample stage once on a pixel surface of 10 to 500 pixel square in a range of 10 μm to 500 μm square. The signal intensity in each pixel in the specific mass number obtained here can be taken out and arranged according to each coordinate to obtain an image.

In both TOF-SIMS and MALDI, positive ions are preferably detected when a target constituent is a protein or a lipid, and on the contrary, negative ions are preferably detected when the target constituent is an oligomer such as DNA and RNA or a fragment of a sugar chain, although not particularly limited to these conditions. Measurement of both positive and negative ions may be performed in the same measurement range to obtain information on many constituents. Further, in order to facilitate mass spectroscopy, particularly when the target constituent is a protein, an analyte sample may be subjected to pretreatment such as previous addition of a digestive enzyme or a sensitizing material thereto. However, this requires the utmost care so that the distribution of the target constituent may be maintained and may not be spread.

(4) The Step of Determining the Region to which the Pixels Belong

In the present invention, the analyte is mainly a tissue section, and the region to which a pixel belongs can be selected, for example, from the intracellular, nuclear, and extracellular regions. Note that the intracellular region refers to a part surrounded by a cell membrane and may or may not include the cell membrane. Further, the intracellular region may or may not include the nucleus. Furthermore, a cell organelle such as microsome, Golgi body, endosome, lysosome, mitochondrion, and peroxisome, or a bone tissue, and a fat tissue may be specified as a region.

The region to which a pixel belongs may be determined from the shape based on the observation in the step (1) or the following steps may be added thereto. That is, the region to which each pixel belongs is specified by obtaining a digital image of an analyte sample in the measurement range using a higher-precision optical microscope and distinguishing a sectional outline of a cell in the analyte according to the contrast difference of the digital image. In the observation by an optical microscope, a reflection type microscope is usually used, but when HE staining or fluorescent staining is applied to an analyte sample, a fluorescence microscope may also be used.

Alternatively, the region to which a pixel belongs may be determined based on the two-dimensional distribution of the mass spectrum obtained in the step (3). In this case, the region is determined based on the two-dimensional distribution of the signal intensity of specific mass from the result of the mass spectroscopy in the step (3). The specific mass is desirably the mass corresponding to a fragment ion of a lipid component which can indicate the distribution of the sectional outline of a cell or a cell membrane and a fragment ion of a protein, a peptide, DNA, RNA, and the like known to be largely present in the position of the nucleus of a cytoplasmic region (hereinafter referred to intracellular region). More specifically, the specific mass is desirably the mass corresponding to a fragment ion of actin, tubulin, and GAPDH in the intracellular region, histone and nucleic acid in the nucleus region, and albumin and cytokine in the extracellular region. It is possible to determine to what type of region the specific pixel belongs based on the two-dimensional distribution image of such signal intensity.

The signal intensity may be corrected by multiplying each image by the signal intensity of Na for each pixel of the above respective images in order to remove the influence on the ion detection sensitivity exerted by a salt impurity.

In any case, when two or more region components overlap in one pixel in the region to which the pixel belongs, it is also possible to calculate the area ratio of each region component contained in the pixel and use the area ratio in a weighted form at the time of applying the internal standard in the next step.

(5) The Step of Determining an Internal Standard Material for Mass Spectroscopy of the Pixels The internal standard of a pixel can be determined by an attribute of the region to which the pixel belongs. Note that the internal standard material is desirably selected so that it satisfies the following two conditions:

(i) The material is stably present in each of the cross-sectional intracellular region, cross-sectional nuclear region in a cell, or extracellular region; and (ii) The abundance is at a level in the range of from 10 to $10^3$ pieces/$\mu m^3$.

Specifically, proteins, peptides, amino acids, lipids, phosphoric acids, sugar chains, and nucleic acids are preferably applied as the internal standard material. More specifically, the preferably applied internal standard materials include actin, tubulin, and GAPDH when the region belongs to the intracellular region; histone and nucleic acid when the region belongs to the nucleus; and a protein molecule such as albumin and cytokine when the region belongs to the extracellular region.

(6) The Step of Calculating the Normalized Intensity of the Mass Derived from a Target Constituent from the Signal Intensity of the Mass Derived from the Target Constituent in the Mass Spectrum of Pixels and the Signal Intensity of the Mass Derived from an Internal Standard Material The signal intensity of a target constituent is normalized and calculated for each pixel by applying "the signal intensity of a target constituent and the signal intensity of the assigned internal standard material" to the mass spectrum obtained in the step (3) based on the internal standard material assigned to each pixel determined in the step (5). At this time, the signal intensity of the assigned internal standard material does not need to be the intensity of the molecule of the internal standard material itself but may be a signal of what can specify the internal standard material. For example, if a protein is subjected to digestive treatment as pretreatment in the step (2), the detection signal of a fragment molecule produced by digesting the protein can be used as a signal of the internal standard material.

For example, the ratio (Signal intensity of a target constituent)/(signal intensity of the assigned internal standard material) can be used as the normalized signal intensity.

Moreover, a further calculation may be made for the value of the normalized signal intensity, for example, by multiplying the ratio (signal intensity of a target constituent)/(signal intensity of the assigned internal standard material) by a suitable constant such as the weight of the assigned internal standard material or the like.

As mentioned above, when a plurality of internal standard materials is assigned to one pixel, the signal intensity may also be corrected by weighting according to each occupied area ratio in a pixel.

Further, when there are a plurality of target constituents to be subjected to normalization processing, the present step may be simultaneously performed to the plurality of target constituents.

(7) The Step of Constructing a Two-Dimensional Distribution Image in the Measurement Range of the Normalized Signal Intensity of the Mass Derived from the Target Constituent For reconstructing the image, the normalized signal intensity of each pixel obtained in the step (4) is formed as a two-dimensional distribution image based on the position of each pixel in the measurement range.

Further, there may be a plurality of target constituents for reconstructing the image as described above.

EXAMPLES

Hereinafter, the present invention will be more specifically described with reference to Examples. The following specific examples are examples of the best embodiments of the present invention, but the present invention is not limited to such specific modes.

Example 1

Hereinafter, there is shown an example in which a tissue section is used as an analyte and an image is acquired by the TOF-SIMS method.

A silicon (Si) substrate containing no impurities is washed with acetone, ethanol, and deionized water, in this order, on which 100 nm of gold (Au) is deposited to form an analytical substrate.

In the present Example, a diseased tissue section is used as an analyte. A diseased tissue is embedded in an OCT compound, is frozen, and is then cut into a thickness of about 4 μm with a microtome to obtain a section. The resulting section is arranged on the substrate which has been previously installed and cooled in the microtome so that an analysis surface faces upward. The section is fixed to the substrate by pressing the edges thereof with a wool brush to be adhered thereto. After the sample is freeze-dried, 10 μL of a trypsin solution having a proper concentration are dropped on the surface of the sample. The sample is digested overnight in the state where humidity is held constant at 37° C. to cause fragmentation of the protein component of sample constituents.

Figure 1:
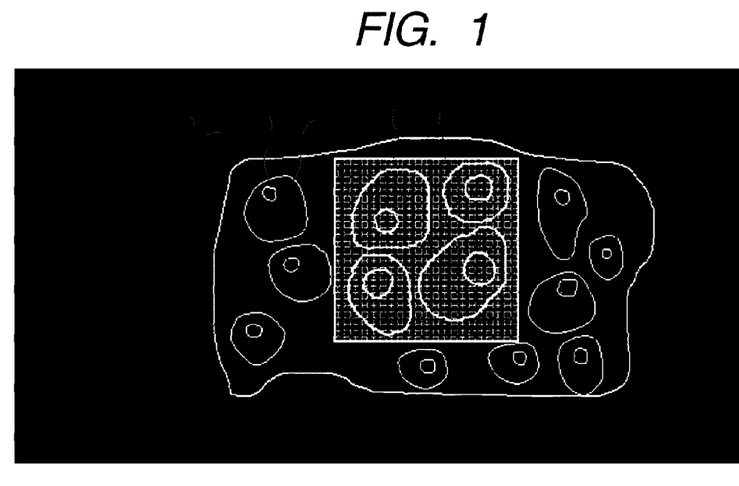
FIG. 1 illustrates a schematic diagram of the optical microscope image of an analyte and the pixel coordinates XY in the measurement range.

The tissue section which is fixed on the substrate and has been subjected to digestion treatment as described above is introduced into a TOF-SIMS instrument. The section is observed under a microscope attached to the instrument, and the measurement range is selected based on the contrast difference of the microscope image. At the same time, the number of pixels constituting the measurement range is determined on software attached to the TOF-SIMS instrument. The sample stage position at this time is recorded as XY coordinates. In addition, the optical microscope image in which the outer frame line of the measurement range is superimposed on the tissue section is stored as digital data. The position of the measurement range in the image is recorded as XY coordinates. FIG. 1 illustrates a schematic diagram illustrating the optical microscope image at this time and the situation of the acquisition of pixel coordinates XY in the measurement range. In FIG. 1, reference numeral 1 denotes a tissue section, reference numeral 2 denotes a cell, reference numeral 3 denotes a nucleus, reference numeral 4 denotes measurement range (constituted from 128×128 measurement pixels) and reference numeral 5 denotes a measurement pixel. In the present Example, TOF-SIMS analysis and analytical work are performed under the following conditions using a TOF-SIMS type 5 instrument (trade name) manufactured by ION-TOF and IONSPEC (trade name) and IONIMAGE (trade name) manufactured by ION-TOF as the software attached thereto. Note that in order to obtain a clearer measurement range, the cell nucleus and membrane parts in the tissue section sample may be dyed after the TOF-SIMS measurement before obtaining an optical microscope image.

Primary ion: 25 kV $Bi_3^+$, 0.3 pA (pulse current value), sawtooth scan mode

Pulse frequency of primary ion: 2.5 kHz (400 μs/shot)

Pulse width of primary ion: about 0.8 ns

Diameter of primary ion beam: about 0.8 μm

Measurement range: 26 μm×26 μm

Number of pixels of secondary ion to be measured: 128×128

Integration time: 128 times scanning (about 500 seconds)

Detection mode of secondary ion: positive ion

Figure 2:
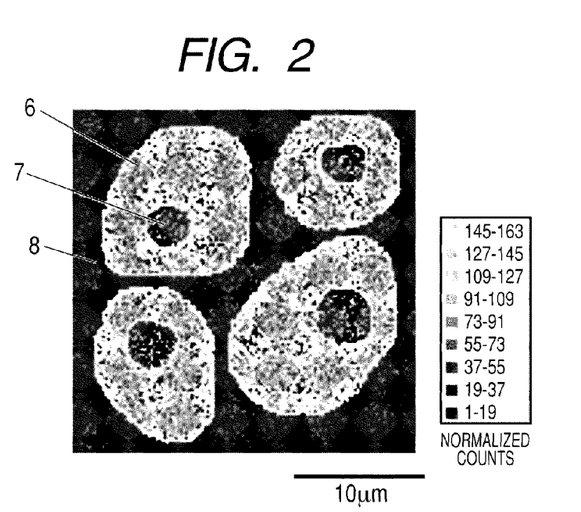
FIG. 2 illustrates a corrected lipid fragment secondary ion signal distribution (128×128 pixels) for specifying the "region to which a pixel belongs".

The internal standard material is determined for each pixel from the two-dimensional distribution of the obtained mass spectrum and the information on the "region to which a pixel belongs". At this time, it is not necessary to continuously perform the measurement of a sample and analysis processing to be described below, but the information on the two-dimensional distribution of the mass spectrum measured previously may be stored as electronic data. At that time, if the information necessary to discriminate the "region to which a pixel belongs" in the measurement is also separately stored and can be optionally referred, it is also possible to perform only the analysis processing operation, for example, later on a computer different from the TOF-SIMS instrument. Detail will be described in the following Example 2. In the present Example, for discriminating the "region to which a pixel belongs", there is used, as a mass spectrum two-dimensional distribution, a signal distribution which has been normalized by multiplying the signal intensity of the lipid fragment ion (Phosphocholine: m/z 184) detected from a cell membrane by the signal intensity of sodium ion ($Na^+$: m/z 23) in each pixel and a suitable constant in order to remove the influence of a salt. As illustrated in FIG. 2, the position corresponding to each pixel coordinate XY (0 to 127, 0 to 127) specifies one of the (a) intracellular region (reference numeral 6), (b) nuclear region (reference numeral 7), and (c) extracellular region (reference numeral 8) using the cell membrane part except the cell outline and cell nucleus drawn by the signal intensity distribution of the lipid fragment as the main standard. In order to clearly distinguish between the regions, the boundary of the specified regions is illustrated with a white closing line in FIG. 2. Note that in the present Example, the pixel in which a plurality of regions are contained is not set. In specifying the region to which a pixel belongs, each region of (a) to (c) to which each pixel coordinate XY belongs may be specified from the optical microscope photograph illustrated in FIG. 1 obtained as described above.

Figure 3:
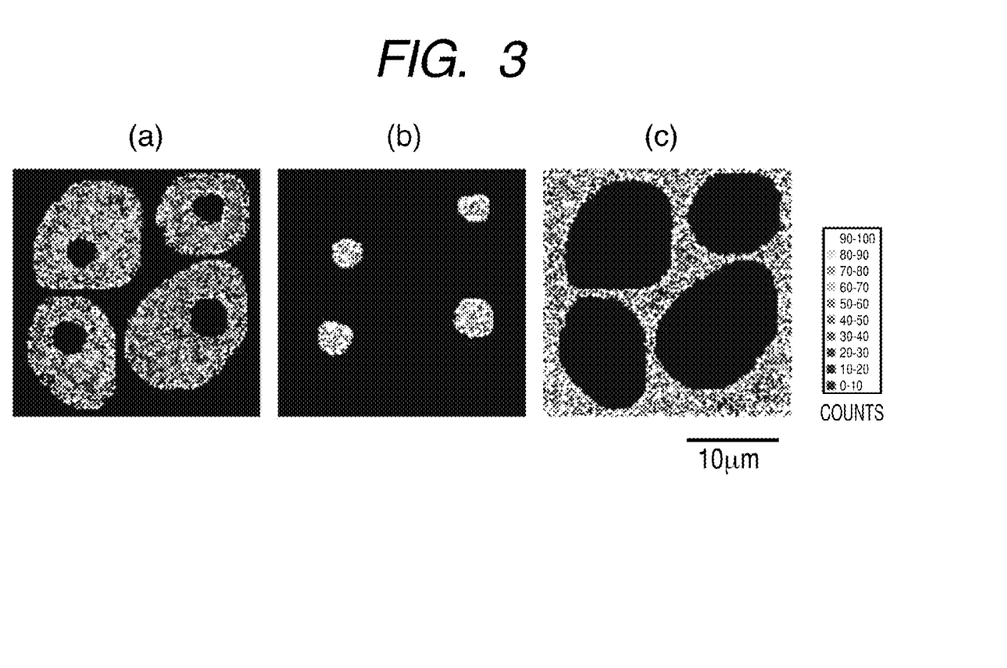
FIGS. 3(a), 3(b) and 3(c) each illustrate a two-dimensional signal distribution (128×128 pixels) of the signal intensity of each internal standard material assigned to (a) intracellular region (b) nuclear region and (c) extracellular region, respectively, specified as the "region to which a pixel belongs".

Then, a suitable internal standard material is assigned to each of the "regions to which a pixel belongs" (a) to (c) in each pixel coordinate XY. In the present Example, the following fragment ions are respectively assigned as the internal standard material: the fragment ion of the protein β-actin (amino acid sequence LDLAGR+H: m/z 644) in the region (a); the fragment ion of the protein histone (LLGR+H: m/z 457) in the region (b); and the fragment ion of the protein serum albumin (FPK+Na: m/z 413) in the region (c). The two-dimensional distribution of the signal intensity of the internal standard material assigned to each of the regions (a) to (c) is indicated for each region in FIG. 3. The fragment ion of each of the above proteins used here is a material specifically detected from each parent protein in the TOF-SIMS method. Therefore, the distribution and the amount of the protein which is the original internal standard can be indirectly expressed, and it is suitable as a detection signal used for normalization. However, internal standard materials and the fragment ions thereof are not necessarily limited to those described above, but suitable internal standard materials and fragment ions thereof may be used depending on a measuring method and the state of a target constituent and a sample.

Figure 4:
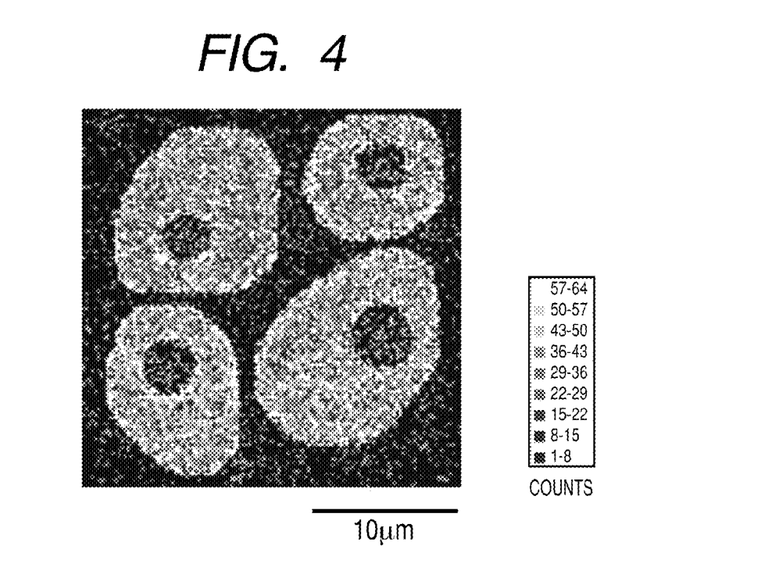
FIG. 4 illustrates a distribution (128×128 pixels) of the secondary ion signal intensity of protein C which is obtained by measurement and is not subjected to normalization processing.

In the present Example, the protein cytokeratin 19 (hereinafter, referred to as protein C) which is largely developed specifically in the intracellular region of diseased cells is used as the target, and the signal intensity of the fragment ion (IRDWYQK+H: m/z 1008) specifically detected from the protein C is used for analysis. FIG. 4 illustrates the distribution of the fragment ion signal intensity which is not subjected to normalization processing.

Figure 5:
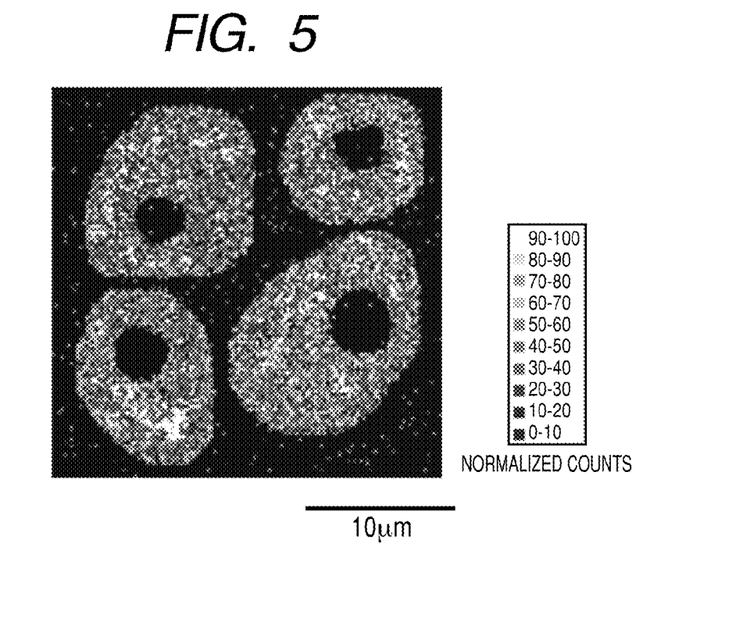
FIG. 5 illustrates a two-dimensional distribution (128×128 pixels) of the signal intensity of protein C in which the "region to which a pixel belongs" is specified and normalization processing has been performed by assigning an internal standard material to each pixel.

Next, the measurement image is constituted based on the intensity value of the protein C fragment ion normalized as described above. FIG. 5 illustrates the results. In FIG. 5, since the signal intensity is normalized, the variation in the measurement for each pixel has been corrected. Further, in FIG. 5, if the detection efficiency difference between fragment ion species is ignored, the approximate abundance of protein C can also be estimated from the abundance of the material used as the internal standard and the normalized ion intensity value. In the case of the present Example, the abundance of protein C in the plane of the cross-sectional intracellular region can be estimated to be about 30 to $1\times10^2$ pieces/$\mu m^2$ by estimating the value from the fact that the abundance of the protein β-actin used as the internal standard in the cross-sectional intracellular region (a) is regarded to be about $10^5$ to $10^6$ pieces per cell. Further, the abundance of protein C in the plane of the cross-sectional intracellular region will be 4 to 100 pieces/Count, in terms of the amount per Count of the normalized signal intensity in FIG. 5.

Comparative Example

Figure 6A:
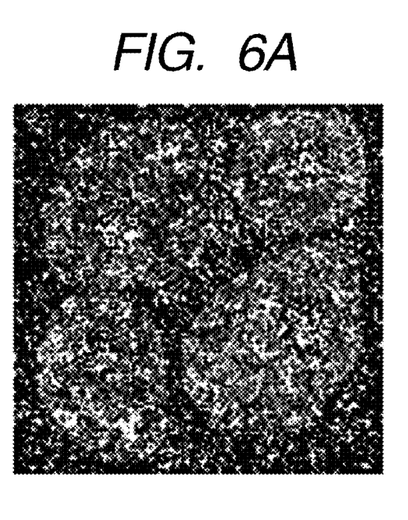
FIGS. 6A and 6B each illustrates a two-dimensional distribution of the signal intensity of protein C in which the "region to which a pixel belongs" is not specified and normalization has been performed by applying the same internal standard material to all the pixels in the measurement range (128×128 pixels). The signal intensity is normalized by using β-actin (FIG. 6A) and by a lipid component (FIG. 6B) respectively as an internal standard material.
Figure 6B:
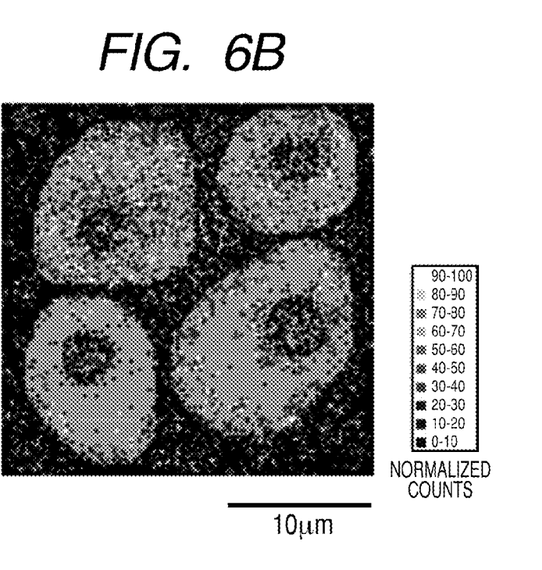

FIGS. 6A and 6B respectively illustrate, for comparison purposes, the results in the case of reconstructing the measurement image by the normalization using the same internal standard material (one of the protein β-actin fragment ion and lipid fragment ion as described above) for all the pixels in the whole measurement range. In normalization, when a division error arises from the fact that the signal intensity of the internal standard is zero, a correction is made by suitably adding a small value (for example, 1) to the signal of the internal standard.

When the fragment ion of the protein β-actin is used as the internal standard, the image of FIG. 6A is obtained. Since the fragment ion signal intensity of the same internal standard material was used for the pixels of the whole measurement range, the signal intensity of the protein C fragment ion is a value higher than the signal intensity to the actual abundance, for example, in the extracellular and nuclear regions where the protein β-actin is seldom present. In FIG. 5, the extracellular normalized signal intensity shows 0-10 in almost all pixels. In FIG. 6A, on the other hand, the extracellular normalized signal intensity extremely varies between 0-10 and 90-100 by the pixel. FIG. 6A lacks correlation with the abundance of the actual protein C because protein C is originally present only in the intracellular region.

When the lipid fragment ion is used as an internal standard, FIG. 6B will be obtained. After all, in the extracellular and nuclear regions in which lipid is seldom present, the normalization signal intensity is indicated lacking the correlation with the actual abundance.

Since FIG. 5 is normalized using the internal standard suitable for each region, the contrast between regions is adjusted to create clearer images than FIGS. 6A and 6B.

Table 1 shows the signal intensity (Counts or Arbitrarily Unit) and its distribution percentage of protein C in each of the cross-sectional intracellular region, the cross-sectional nuclear region in a cell, and the extracellular region, in the signal distribution of protein C (FIG. 4) which has not been subjected to normalization processing and the signal distributions of protein C (FIG. 5, FIGS. 6A and 6B) obtained by the normalization processing methods in Example 1 and Comparative Example as described above. Table 1 shows that in the signal distribution of protein C (FIG. 5) obtained by the normalization procedure in the above Example, the signal of protein C is detected from the cross-sectional intracellular region at a high percentage of 97% or more of all the signals. This shows the presence distribution which suits the original distribution of protein C that is mostly present in the intracellular region. On the other hand, in the signal distribution (FIG. 4) which has not been subjected to normalization processing and the signal distributions (FIGS. 6A, 6B) obtained by the normalization processing method in Comparative Example, the detection rate in the cross-sectional intracellular region is not so high and the signal is detected even in the cross-sectional nuclear region and the extracellular region. These distributions do not correctly show the original distribution of protein C. The above results also show that suitable signal normalization is performed by the procedure of the present Example. Thus, it is very difficult to visualize the protein at a cellular level, and it is also difficult to obtain a stable quantitative result, by using the conventional normalization procedure in which the internal standard material is applied to the whole pixels in the measurement range of an analyte without specifying the "region to which a pixel belongs".

As described above, Example 1 and Comparative Example verify that the information on the two-dimensional distribution state of a specific protein present in a diseased tissue section can be obtained more quantitatively by subjecting the TOF-SIMS measurement results to the normalization of the target constituent by applying the internal standard material according to the "region to which a pixel belongs" and performing image reconstruction.

Example 2

Hereinafter, there is illustrated a method of holding information on the mass of constituents in an analyte obtained from a determined measurement range as electronic data and using computer software to the electronic data to semi-automatically form a two-dimensional distribution image of the target constituent.

The data used for processing is the electronic data that stores the mass spectrum two dimensional distribution obtained by measuring the trypsin-digested tissue section obtained in Example 1. The procedure of processing is as follows.

(Step 1) The number of pixels in the measurement range is specified. The two-dimensional distribution data of this mass spectrum is constituted from 128×128 measurement pixels in the XY direction. For the purpose of reducing processing time, the measurement range is divided into 64×64 pixels by redefining 2×2 measurement pixels in the XY direction as one pixel. And the number of 0 to 63 is newly applied to each pixel in the XY coordinates.

(Step 2) The mass spectrum is extracted from each pixel, and each spectrum is held in a memory region together with the XY coordinates as individual data.

Figure 7:
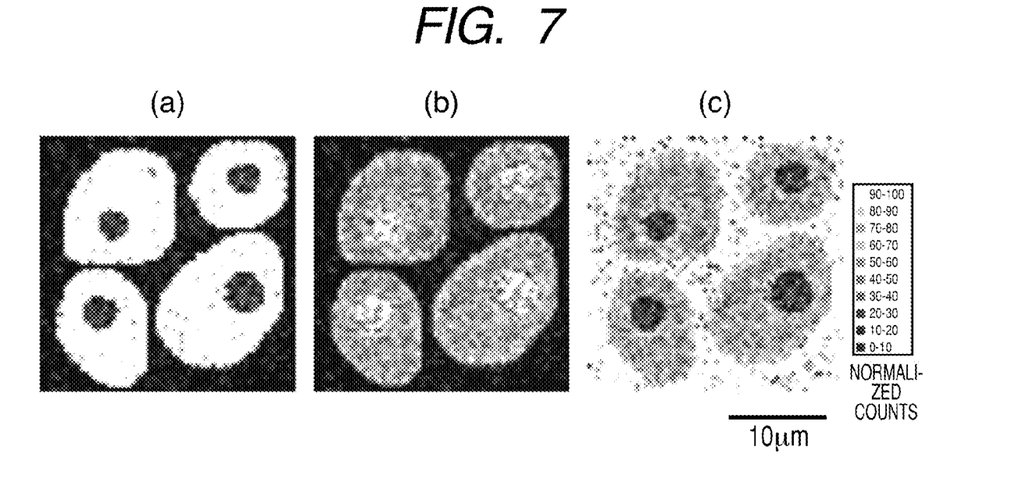
FIGS. 7(a), 7(b) and 7(c) each illustrate a two-dimensional distribution (64×64 pixels) of the signal intensity of each internal standard material assigned to (a) intracellular (b) nuclear and (c) extracellular, respectively, specified as the "region to which a pixel belongs".

(Step 3) The region to which each pixel belongs is determined from the obtained mass spectrum. (1) Each of the ion peaks: the fragment ion of the protein β-actin (amino acid sequence LDLAGR+H: m/z 644) for (a), the fragment ion of the protein histone (LLGR+H: m/z 457) for (b), and the fragment ion of the protein serum albumin (FPK+Na: m/z 413) for (c), used in Example 1, is specified as a standard for discriminating regions. (2) The signal intensity for each of (a), (b), and (c) in the mass spectrum of each pixel is calculated. The values of the signal intensity are stored in the array P (X, Y, N) by designating the ion peaks: (a), (b), and (c) as N=1, 2, and 3, respectively, and using the coordinates XY of each pixel as the index. (3) Each average intensity value for each of the ion peaks: (a), (b), and (c) in all the measurement pixels is determined, and the resulting value is stored in the array Q (N). (4) In all the pixels, N is changed from 1 to 3 in this order, and the case of P (X, Y, N)>Q (N) is retrieved. The region to which each pixel belongs is any one of the intracellular region when N=1, that is, (a), the nuclear region when N=2, that is, (b), and the extracellular region when N=3, that is, (c). When the retrieved result does not correspond to any of the above cases, the processing in the subsequent steps 4 to 6 are omitted because the pixel has no region to which it belongs. For reference purposes, FIG. 7 illustrates the ion peak intensity (normalized value) of each of (a), (b), and (c) in 64×64 pixels.

(Step 4) The internal standard material to be applied to the normalization calculation is determined for the pixel whose region to which it belongs has been determined, in accordance with each region to which the pixel belongs. In the present Example, the protein β-actin and its fragment ion (LDLAGR+H: m/z 644) for (a), the protein histone and its fragment ion (LLGR+H: m/z 457) for (b), the protein serum albumin and its fragment ion (FPK+Na: m/z 413) for (c) used for discriminating regions as described above are assigned as the internal standard materials and fragment ions derived from these materials to the intracellular region (a), the nuclear region (b), and the extracellular region (c), respectively, to which a pixel belongs.

Figure 8:
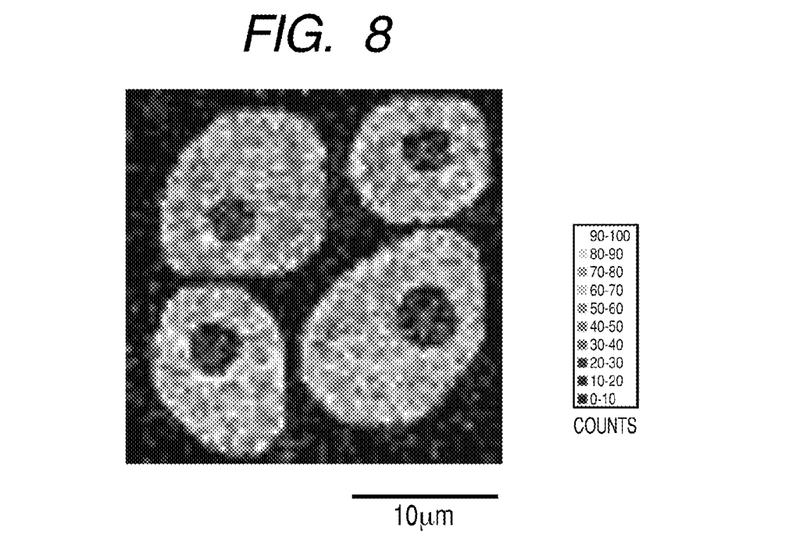
FIG. 8 illustrates a distribution (64×64 pixels) of the secondary ion signal intensity of protein C which is obtained by measurement and is not subjected to normalization processing.

(Step 5) The normalized signal intensity is calculated using the signal intensity of the mass derived from the target constituent of the mass spectrum in each pixel and the intensity of the fragment ions derived from the internal standard materials assigned in Step 4. The resulting normalized value is stored in the array storage region R (X, Y) indicated by the XY coordinates of the pixel. In the present Example, similar to Example 1, protein C is used as a target constituent, and the signal intensity of its fragment ion (IRDWYQK+H: m/z 1008) is used for the target of normalization. FIG. 8 illustrates the distribution of the signal intensity of the protein C fragment ion before normalization.

Figure 9:
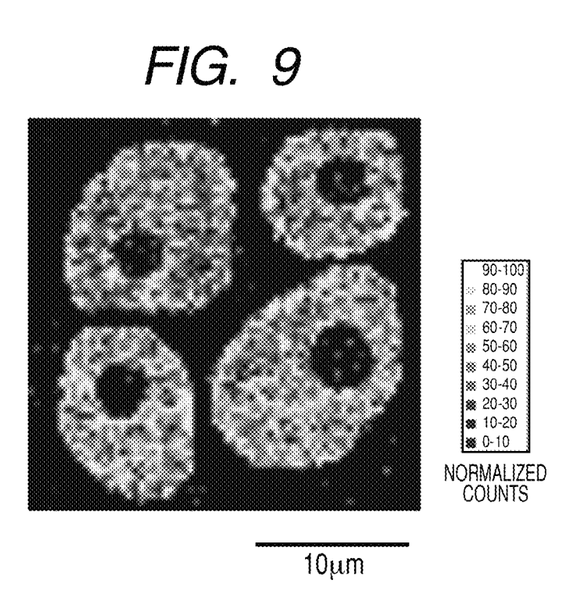
FIG. 9 illustrates a two-dimensional distribution (64×64 pixels) of the signal intensity of protein C in which the "region to which a pixel belongs" is semi-automatically specified and normalization has been performed by assigning an internal standard material to each pixel.

(Step 6) The two-dimensional distribution image in the measurement range is constructed using the normalized values of the mass signal intensity derived from the target constituent. The two-dimensional distribution image of the constructed normalized mass signal is constructed in FIG. 9.

Figure 10A:
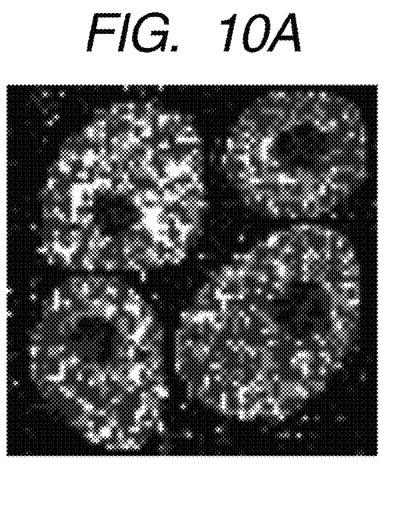
FIGS. 10A and 10B illustrate two-dimensional distributions of the signal intensity of protein C in which the "region to which a pixel belongs" is not specified and normalization has been performed by applying the same internal standard material to all the pixels (64×64 pixels). The signal intensity was normalized by using β-actin for FIG. 10A and a lipid component for FIG. 10B, respectively, as an internal standard material.
Figure 10B:
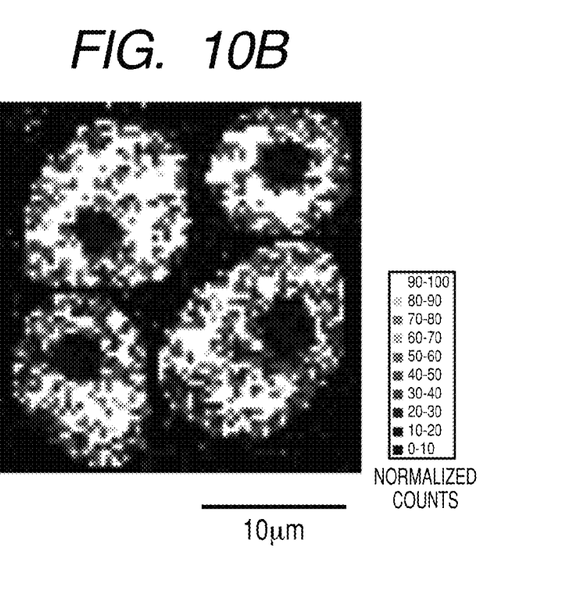

For comparison purposes, there are shown the results in the case of performing the normalization using the same internal standard material for all the pixels in the whole measurement range. One of the protein β-actin fragment ion (LDLAGR+H: m/z 644) and the lipid fragment ion (Phosphocholine: m/z 184) as described above is used as the internal standard material. The results are shown in FIGS. 10A and 10B, respectively. In normalization, when a division error arises from the fact that the signal intensity of the internal standard is zero, calculation is previously skipped and the value of 0 (zero) is input into the array storage region R (X, Y). It is apparent that by the above processing, the signal distribution (FIG. 9) that is normalized using the internal standard suitable for each region correctly indicates the original distribution of protein C that is present in the intracellular region as compared with the signal distributions (FIGS. 10A and 10B) normalized by other methods.

TABLE 1

Signal distribution comparison of protein C for each region by various normalization processing methods

|  | (a) Cross-sectional intracellular region | (b) Cross-sectional nuclear region | (c) Extracellular region |
|---|---|---|---|
| Signal intensity (Counts) and distribution percentage for each region in the signal distribution without normalization processing in FIG. 4 | 1,456,932 86.5% | 56,372 3.3% | 170,576 10.1% |
| Signal intensity (arb. unit) and distribution percentage for each region in the signal distribution normalized by assigning the internal standard to each pixel in FIG. 5 | 1,096,741 97.4% | 1,569 0.1% | 27,648 2.5% |
| Signal intensity (arb. unit) and distribution percentage for each region in the signal distribution normalized in the whole region by actin in FIG. 6A. | 1,072,125 60.6% | 52,593 10.6% | 211,985 28.8% |
| Signal intensity (arb. unit) and distribution percentage for each region in the signal distribution normalized in the whole region by lipid ionic strength in FIG. 6B. | 2,564,922 80.2% | 447,198 3.9% | 1,217,817 15.9% |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-096091, filed on Apr. 10, 2009, which is hereby incorporated by reference herein in its entirety.

The invention claimed is:

1. A method of forming a two-dimensional distribution image of a target constituent in constituents of a tissue section based on information on the mass of constituents of the tissue section comprising:
   determining a region to which the constituents belong to be at least one of an intracellular region, a nuclear region, and an extracellular region;
   calculating, for each region determined in the previous region determination, a normalized intensity of the mass derived from the target constituent from a mass signal intensity derived from the target constituent in a mass spectrum of the constituents and a mass signal intensity derived from an internal standard material in the constituents; and
   forming the two-dimensional distribution image of the target constituent based on the normalized intensity of the mass derived from the target constituent,
   wherein, as the internal standard material, (i) any one of actin, tubulin, and GAPDH is used in the intracellular region, (ii) one of histone and nucleic acid is used in the nuclear region, and (iii) one of albumin and cytokine is used in the extracellular region.

2. The method according to claim 1, wherein the mass spectrum of the constituents is measured by the TOF-SIMS method.

3. The method according to claim 1, wherein the information on the mass of the constituents is based on the information for each pixel having a length of one side of 5 μm or less.

* * * * *